United States Patent [19]

Okuno et al.

[11] 3,932,459
[45] Jan. 13, 1976

[54] NOVEL CYCLOPROPANECARBOXYLIC ACID ESTERS

[75] Inventors: Yoshitoshi Okuno, Toyonaka; Masachika Hirano, Ashiya; Isao Ohno, Minoo; Hisami Takeda, Takarazuka; Osamu Magara, Osaka; Nobushige Itaya, Nishinomiya; Toshio Nishioka, Takarazuka; Toshio Mizutani; Nobuo Ohno, both of Toyonaka; Takashi Matsuo, Nishinomiya, all of Japan

[73] Assignee: Sumitomo Chemical Company, Limited, Osaka, Japan

[22] Filed: July 25, 1974

[21] Appl. No.: 491,636

[30] Foreign Application Priority Data
July 30, 1973 Japan.............................. 48-86121

[52] U.S. Cl...................... 260/332.2 A; 260/329 F
[51] Int. Cl.²......................................... C07D 333/24
[58] Field of Search............................. 260/332.2 A

[56] References Cited

OTHER PUBLICATIONS

Itaya, "Chem. Abstracts" (1970), Vol. 72, p. 121192j.
Hartough, "The Chemistry of Heterocyclic Compounds," (1952) (Thiophene and Its Derivatives) pp. 43, 44.
Roberts, "Base Principles of Organic Chemistry" (1964), P. 389.

*Primary Examiner*—James O. Thomas, Jr.
*Assistant Examiner*—A. Siegel
*Attorney, Agent, or Firm*—Stevens, Davis, Miller & Mosher

[57] ABSTRACT

A new cyclopropanecarboxylic acid ester represented by the formula,

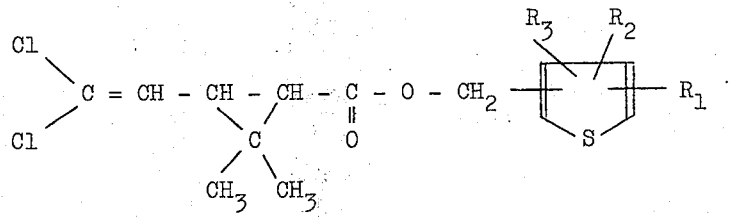

wherein $R_1$ is alkyl having up to four carbon atoms, alkenyl having up to five carbon atoms, cycloalkenyl having up to six carbon atoms, alkenyl having up to five carbon atoms, benzyl, phenoxy or halogen; $R_2$ and $R_3$ are hydrogen, halogen or methyl; and any adjacent two of $R_1$, $R_2$ and $R_3$ may combine to form polymethylene, which is useful as insecticides and acaricides having a strong insecticidal activity but a low toxicity to mammals, in agriculture, horticulture as well as public health.

3 Claims, No Drawings

NOVEL CYCLOPROPANECARBOXYLIC ACID ESTERS

The present invention relates to
1. a new cyclopropanecarboxylic acid ester represented by the formula (I),

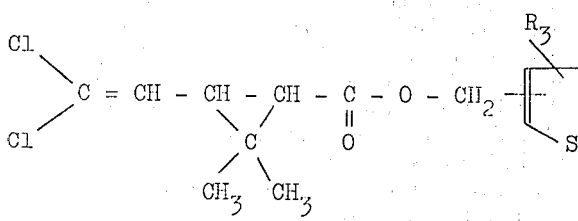

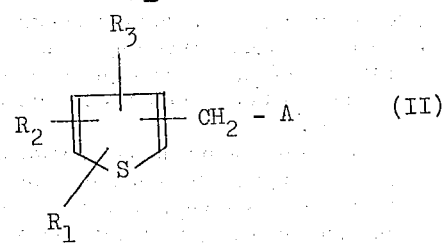

wherein $R_1$, $R_2$ and $R_3$ are the same as defined above wherein $R_1$ is an alkyl having up to four carbon atoms, alkenyl having up to five carbon atoms, cycloalkenyl having up to six carbon atoms, alkynyl having up to five carbon atoms, benzyl, phenoxy group, or a halogen atom; $R_2$ and $R_3$ are each a hydrogen, halogen atom or a methyl group; and the two among $R_1$, $R_2$ and $R_3$ which are adjacent to each other may combine at the ends thereof to form a polymethylene linkage,
2. preparation of said ester and (3) insecticides and acaricides characterized by containing said ester as an active ingredient.

An object of the present invention is to provide insecticides and acaricides, at a low price, which have low toxicity to mammals but have a strong insecticidal activity, for agriculture and horticulture as well as public health.

Among the insecticides which are now in common use, those which can safely be used due to their harmlessness to mammals in spite of their immediate effect upon insects, are pyrethrum extracts (containing pyrethrin) and synthetic allethrin which is a homologue of pyrethrin. However, the pyrethrum extracts are relatively expensive and so their use is often limited irrespective of their usefulness.

The inventors prepared various cyclopropanecarboxylic acid esters experimentally, checked the biological activity and found that the esters represented by formula (I) have an excellent activity for killing sanitary pests such as houseflies, mosquitoes, cockroaches and others; harmful insects to agriculture and horticulture; and mites. In addition, the present esters have a higher insecticidal activity than that of corresponding chrysanthemic acid esters, irrespective of low toxicity to mammals and can be prepared at a low cost. Thus, the inventors completed the present invention.

The insecticides according to the present invention are widely used for pesticides and furthermore they are also very useful for controlling harmful insects to stored cereals, agriculture and wood and forest, since they have a high controlling effect upon the insects. Particularly, low toxicity of the present esters makes it possible to use them for agricultural crops before harvest, green-house cultivation, household horticulture and food-packaging.

The cyclopropanecarboxylic acid esters represented by formula (I) are new compounds which were first discovered by the inventors and can be prepared by reacting an alcohol represented by the formula (II), and A is a hydroxyl group or halogen atom, or its halide with cyclopropanecarboxylic acid represented by the formula (III),

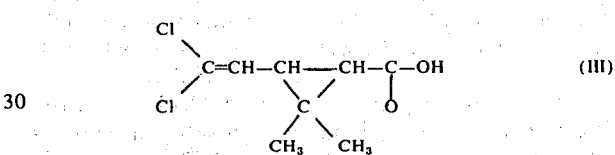

or its reactive derivatives, if necessary, in the presence of suitable solvents, reaction-auxiliary agents or catalysts.

The reactive derivatives of cyclopropanecarboxylic acid (III) include acid halide, acid anhydride and alkali metal salt thereof.

It is a matter of course that the esters of formula (I) include a geometrical isomer resulting from the steric configuration of carboxylic acid (III) and an optical isomer resulting from the asymmetric carbon atom of alcohol (II) and carboxylic acid (III).

The embodiments of the present invention will be illustrated in more details with reference to the preparation of the present compounds.

In a first embodiment of the method, the required ester (I) is obtained by reacting the alcohols of formula (II) with the carboxylic acids of formula (III), or acid halides or acid anhydrides thereof.

When the acid itself is used, the reaction is completed under conditions of dehydration. Thus, the reaction is carried out under heating in the presence of an acid catalyst such as a mineral acid or p-toluenesulfonic acid, and an azeotropic solvent such as benzene or toluene. Alternatively, the reaction may well be carried out with or without heating in an inert solvent such as benzene or petroleum ether, in the presence of a dehydrating agent such as dicyclohexylcarbodiimide.

When the acid halide is used, the reaction can be sufficiently carried out at room temperature using an organic tertiary amine such as pyridine or triethylamine as an acid-binding agent. The acid halide used may be any within the scope of the present invention, but the acid chloride is usually used. In the reaction, the use of solvents is preferable to allow the reaction to proceed smoothly, and an inert solvent such as benzene, toluene or petroleum benzin is generally used.

When the acid anhydride is used, the reaction can be carried out at room temperature to form an objective ester of formula (I) without particularly using any reaction-auxiliary agent. Warming of the reaction system and the use of inert solvents are preferred in order to allow the reaction to proceed smoothly, but they are not essential.

In the second embodiment of the process, the ester of formula (I) is prepared from the compound of formula (II) wherein A is a halogen atom. Among the halogen atoms represented by A, chlorine or bromine atom is, in general, most commonly used, but other halogen atoms may be selected. The other reactant is an alkali metal or tertiary amine salt of the carboxylic acid of formula (III), which may be prepared prior to the reaction, or formed in situ in the reaction system by adding the corresponding bases forming such salts to the reaction mixture. The reaction is preferably carried out in the presence of an inert solvent such as benzene or acetone at a temperature of the boiling point or lower, of the solvent used.

The cyclopropanecarboxylic acid of formula (III) used according to the present invention is disclosed in J. Farkas et al., Chem. Listy 52, 688, 1958 (C. A. 52, 13650, 1958) in which they reported that an allethronyl ester of the acid has an insecticidal activity close to that of chrysanthemic acid ester. The acid can easily be prepared from chloral and isobutene which are available at a low price, and can easily be converted to the reactive derivatives by well known methods which are used for, for example, chrysanthemic acid.

The alcohols represented by formula (II) can easily be obtained by an addition reaction between acetylene or hydrogen cyanide and the corresponding aldehyde. The compound of formula (II) in which A is a halogen atom, can easily be obtained by halogenating the corresponding alcohol of formula (II) in which A is a hydroxyl group.

The present invention will be illustrated with reference to the standard processes, A, B, C and D as follows:

Process A: The reaction of the alcohol and the carboxylic acid halide

In a solution of 0.05 mole of the alcohol in 3 times by volume of dry benzene is dissolved 0.075 mole of pyridine. To the solution is added, at one time, a solution of 0.053 mole of the carboxylic acid chloride in 3 times by volume of dry benzene. Thus, an exothermic reaction proceeds. After being allowed to stand overnight in a tightly sealed container, a small amount of water is added to the reaction mixture to dissolve pyridine hydrochloride precipitated and the aqueous layer formed is separated. The organic layer is successively washed with a 5% aqueous hydrochloric acid, saturated aqueous sodium hydrogen carbonate solution and saturated aqueous sodium chloride solution, dried over anhydrous sodium sulfate and distilled to remove benzene under reduced pressure. The residual liquid is subjected to silica gel chromatography to obtain the purified objective ester.

Process B: The dehydration reaction between the alcohol and the carboxylic acid

To a solution of 0.05 mole each of the alcohol and the carboxylic acid in 3 times by volume of benzene is added 0.08 mole of dicyclohexylcarbodiimide. The reaction mixture is allowed to stand overnight in a tightly sealed container. The reaction is completed on the following day by refluxing for 2 hours and then the objective ester is obtained in the same manner as described in Process A.

Process C: The reaction of the alcohol and the carboxylic acid anhydride

To a solution of 0.05 mole of the alcohol in 3 times by volume of toluene, is added 0.05 mole of the carboxylic acid anhydride prepared by a reaction between the carboxylic acid and acetic anhydride. The mixture is heated at 100°C for 3 hours to complete the reaction, cooled and neutralized with a 10% aqueous caustic soda at a temperature of not higher than 10°C. The carboxylic acid resulting from the reaction is recovered as the sodium salt thereof from the aqueous layer. The organic layer is treated in the same manner as described in Process A to obtain the objective ester.

Process D: The reaction of the carboxylic acid and the halogenated methyl compound A solution of 0.05 mole of the halogenated methyl compound and 0.06 mole of the carboxylic acid in three times by volume of acetone is warmed at 15° to 20°C. To the solution is added dropwise a solution of 0.08 mole of triethylamine in 3 times by volume of acetone while stirring. After the addition, the mixture is refluxed for 2 hours to complete the reaction and cooled. The precipitated triethylamine hydrochloride is filtered off and the filtrate is distilled to remove acetone under reduced pressure. To the remaining liquid is added 3 times by volume of benzene. The mixture is treated in the same manner as described in Process A to obtain the objective ester.

The results obtained by the above standard processes are shown in the following Table. It is a matter of course that the esters according to the present invention are not to be interpreted as limited to the compounds in the Table.

Table

| Example No. | Alcohol or its derivative | Carboxylic acid or its derivative | Process | Compound No. | Compound |
|---|---|---|---|---|---|
| 1 | 5-Benzyl-2-thenyl alcohol | Acid chloride | (A) | (1) | 5-benzyl-2-thenyl 2',2'-dimethyl-3'-(2'',2''-dichlorovinyl)-cyclopropanecarboxylate |
| 2 | 5-Phenoxy-2-thenyl alcohol | Acid chloride | (A) | (2) | 5-Phenoxy-2-thenyl 2',2'-dimethyl-3'-(2'',2''-dichlorovinyl)-cyclopropanecarboxylate |
| 3 | 5-Benzyl-3-thenyl alcohol | Acid chloride | (A) | (3) | 5-Benzyl-3-thenyl 2',2'-dimethyl-3'-(2'',2''-dichlorovinyl)-cyclopropanecarboxylate |

Table-continued

| Example No. | Alcohol or its derivative | Carboxylic acid or its derivative | Process | Compound No. | Compound |
|---|---|---|---|---|---|
| | | Cyclopropanecarboxylic acid ester obtained | | | |

| Yield (%) | Refractive index $n_D^{25}$ | | Elementary analysis | | | |
|---|---|---|---|---|---|---|
| | | | | C | H | Cl | S |
| 94 | 1.5711 | Found (%) Calculated (%) (as $C_{20}H_{20}O_2SCl_2$) | 61.05 60.76 | 5.13 5.10 | 17.81 17.94 | 8.64 8.11 |
| 91 | 1.5648 | Found (%) Calculated (%) (as $C_{19}H_{18}O_3SCl_2$) | 57.17 57.44 | 4.59 4.57 | 17.77 17.85 | 8.21 8.07 |
| 96 | 1.5703 | Found (%) Calculated (%) (as $C_{20}H_{20}O_2SCl_2$) | 60.41 60.76 | 5.03 5.10 | 17.99 17.94 | 8.35 8.11 |

| Example No. | Alcohol or its derivative | Carboxylic acid or its derivative | Process | Compound No. | Compound |
|---|---|---|---|---|---|
| 4 | 4,5-Tetramethylene-2-thenylchloride | Sodium carboxylate | (D) | (4) | 4-5-Tetramethylene-2-thenyl 2',2'-dimethyl-3'-(2'',2''-dichlorovinyl)-cyclopropane-carboxylate |
| 5 | 4,5-Trimethylene-2-thenyl alcohol | Carboxylic acid | (B) | (5) | 4,5-Trimethylene-2-thenyl 2',2'-dimethyl-3'-(2'',2''-dichlorovinyl)-cyclopropane-carboxylate |
| 6 | 5-Allyl-2-thenyl alcohol | Acid anhydride | (C) | (6) | 5-Allyl-2-thenyl 2',2'-dimethyl-3'-(2'',2''-dichlorovinyl)-cyclopropane-carboxylate |
| 7 | 5-Propargyl-2-thenyl alcohol | Acid chloride | (A) | (7) | 5-Propargyl-2-thenyl 2',2'-dimethyl-3'-(2'',2''-dichlorovinyl)-cyclopropane-carboxylate |
| 8 | 5-(2'-cyclopentene-1'-yl)-2-thenyl alcohol | Acid chloride | (A) | (8) | 5-(2'-cyclopentene-1'-yl)-2-thenyl 2'',2''-dimethyl-3''-(2''',2'''-dichlorovinyl)-cyclopropanecarboxylate |

| Yield (%) | $n_D^{25}$ | | C | H | Cl | S |
|---|---|---|---|---|---|---|
| 84 | 1.5522 | Found (%) Calculated (%) (as $C_{17}H_{20}O_2SCl_2$) | 56.91 56.82 | 5.66 5.61 | 19.49 19.74 | 8.96 8.92 |
| 80 | 1.5531 | Found (%) Calculated (%) (as $C_{16}H_{18}O_2SCl_2$) | 55.38 55.65 | 5.15 5.25 | 20.45 20.54 | 9.38 9.29 |
| 71 | 1.5494 | Found (%) Calculated (%) (as $C_{16}H_{18}O_2SCl_2$) | 55.29 55.65 | 5.41 5.25 | 20.33 20.54 | 9.61 9.29 |
| 81 | 1.5526 | Found (%) Calculated (%) (as $C_{16}H_{16}O_2SCl_2$) | 55.72 55.98 | 4.93 4.70 | 20.86 20.66 | 9.51 9.34 |
| 85 | 1.5552 | Found (%) Calculated (%) (as $C_{18}H_{20}O_2SCl_2$) | 58.22 58.51 | 5.43 5.25 | 19.10 18.94 | 8.64 8.35 |

From the comparison by experiment between the esters of cyclopropanecarboxylic acid according to the present invention and the corresponding esters of chrysanthemic acid, it was found that the esters of the present invention have an outstanding insecticidal activity. The results are shown in the following experimental examples. The same tendency was observed with other isomers.

EXPERIMENT 1

The dl-trans isomer of each of the present compounds (1), (2), (4) and (7), and the corresponding dl-trans-chrysanthemic acid esters were individually dissolved in deodorized kerosene to prepare oil sprays of required concentration.

5 ml of each of the oil sprays were sprayed, using Campbel's turn table apparatus ("Soap and Sanitary Chemicals,"Vol. 14, No. 6, 119, 1938). Twenty seconds after spraying, the shutter was opened, and about 100 house-fly adults (*Musca domestica*) per group were exposed to the descending mist for 10 minutes and then transferred to the observation cage. In the cage, the flies were fed and allowed to stand for one day at room temperature.

Thereafter, the number of killed flies was counted to calculate the mortality thereof. The values of $LC_{50}$ (50% lethal concentration) obtained from the mortality are as shown in Table 1.

Table 1

| Test compounds | $LC_{50}$ (mg/100 ml) | Relative efficacy | |
|---|---|---|---|
| dl-Trans isomer of present compound (1) | 9.0 | 4.3 | |
| Corresponding dl-trans-chrysanthemic acid ester | 38.6 | 1.0 | (control) |
| dl-Trans isomer of present compound (2) | 13.5 | 4.0 | |
| Corresponding dl-trans- | | | |

Table 1-continued

| Test compounds | LC$_{50}$ (mg/100 ml) | Relative efficacy | |
|---|---|---|---|
| chrysanthemic acid ester | 54.0 | 1.0 | (control) |
| dl-Trans isomer of present compound (4) | 21.7 | 3.8 | |
| Corresponding dl-trans-chrysanthemic acid ester | 83.4 | 1.0 | (control) |
| dl-Trans isomer of present compound (7) | 20.5 | 4.2 | |
| Corresponding dl-trans-chrysanthemic acid ester | 85.8 | 1.0 | (control) |
| Pyrethrin | 216 | | |

EXPERIMENT 2

Each of the present compounds (1), (2) and (5), and the corresponding chrysanthemic acid esters were individually formulated into a 20% emulsifiable concentrate by usual methods.

10 ml of each of the emulsifiable concentrates which had been diluted with water to the required concentration were sprayed on to four leaves of chinese cabbage grown up to a 3- to 4-leave stage. Then the leaves were placed in a glass Petri dish of 14 cm in diameter and 7 cm high, and 10 fourth instar larvae of diamond-back moth (*Plutella maculipennis*) were liberated therein. After 2 days, the dead and alive were counted. The values of LC$_{50}$ (50% lethal concentration) are as shown in Table 2.

Table 2

| Test compounds | LC$_{50}$ (ppm) | Relative efficacy | |
|---|---|---|---|
| Present compound (1) | 28 | 3.0 | |
| Corresponding chrysanthemic acid ester | 85 | 1.0 | (control) |
| Present compound (2) | 37 | 2.6 | |
| Corresponding chrysanthemic acid ester | 97 | 1.0 | (control) |
| Present compound (5) | 47 | 2.4 | |
| Corresponding chrysanthemic acid ester | 114 | 1.0 | (control) |

EXPERIMENT 3

Each of the present compounds (1) to (7), and the corresponding chrysanthemic acid esters were individually formulated into a 20% emulsifiable concentrate by usual methods.

About 20 rice seedlings were grown up to a 3- to 4-leave stage in a flower pot of 10 cm in diameter, and the 400-fold aqueous diluted solution of each emulsifiable concentrate was applied thereto by means of a turn table.

After air-drying, each pot was placed in a 5 liter glass beaker and covered with gauze at the top. Then, 20 green rice leafhoppers (*Nephotettix cincpriceps*) were liberated therein and the number of knocked down insects were counted at definite time intervals. The values of KT$_{50}$ (a time required for 50% knock-down) are as shown in Table 3.

Table 3

| Test compounds | KT$_{50}$ (minute) |
|---|---|
| Present compound (1) | 17 |
| Corresponding chrysanthemic acid ester | 37 |
| Present compound (2) | 28 |
| Corresponding chrysanthemic acid ester | 45 |
| Present compound (3) | 30 |
| Corresponding chrysanthemic acid ester | 53 |
| Present compound (4) | 24 |

Table 3-continued

| Test compounds | KT$_{50}$ (minute) |
|---|---|
| Corresponding chrysanthemic acid ester | 46 |
| Present compound (5) | 21 |
| Corresponding chrysanthemic acid ester | 43 |
| Present compound (6) | 19 |
| Corresponding chrysanthemic acid ester | 40 |
| Present compound (7) | 15 |
| Corresponding chrysanthemic acid ester | 38 |
| Present compound (8) | 19 |
| Corresponding chrysanthemic acid ester | 40 |

Because of the above-mentioned features, the insecticides and acaricides according to the present invention can widely be used not only for killing harmful insects to public health, for example, houseflies, mosquitoes and cockroaches, and insects harmful to stored cereals, for example, grain mite, indian meal moth and rice weevils, but also for controlling insects injurious to agriculture, horticulture and woods and forests, for example, planthoppers, leafhoppers, armyworms and cutworms, diamond-back moth, tortorixes, aphids, stem-borers, mites and Japanese giant silk moth; animal parasitic lice and mites; and other various species of insects.

The insecticides and acaricides according to the present invention not only cause knock-down and death of harmful insects but also have repellency (the effect of keeping insects away from its host plant). In particular, the insecticides and acaricides can safely be used, due to their low toxicity and harmlessness to mammals, for agricultural crops, especially before they are harvested, household horticulture, green-house cultivation and food-packaging.

In the practical application of the present compounds, they may be applied alone or in combination with carriers when used as pesticides. The present compounds are formulated like the common pesticides into various preparation forms such as emulsifiable concentrates, wettable powders, dusts, granules, fine granules, oil sprays, aerosols, heating fumigants (mosquito coils, electric mosquito killers), thermal fogging agents, non-heating fumigants and baits by the methods well known to the skilled in the art, and are applied in the forms which are suitable for application methods.

Furthermore, the present compounds may be increased in their insecticidal activity when used in combination with known synergists for pyrethroid such as α-[2-(2-butoxyethoxy)-ethoxy]-4,5-methylenedioxy-2-propyltoluene (referred to as piperonylbutoxide), 1,2-methylenedioxy-4-[2-(octylsulfinyl)-propyl]-benzene (referred to as sulfoxide), 4-(3,4-methylenedioxyphenyl)-5-methyl-1,3-dioxane (referred to as sulfoxane), N-(2-ethylhexyl)-bicyclo[2,2,1]hepta-5-ene-2,3-dicarboximide (referred to as MGK-264), octachlorodipropylether (referred to as S-421), or isobornylthiocyano acetate (referred to as Thanite); and with known synergists for allethrin or pyrethrin.

Although the chrysanthemate type compounds are generally a little inferior in resistance to light, heat and oxidation, it is possible that the compounds be formulated into insecticidal compositions having a more stable activity by incorporating, as a stabilizing agent, a proper amount of antioxidants; U. V. absorbers such as phenol derivatives including BHT and BHA, bisphenol derivatives, arylamine derivatives including phenyl-α-naphthylamine, phenyl-β-naphthylamine and condensation products of phenetidine and acetone, and benzophenone compounds.

In addition, the present compounds can be formulated into multi-purpose compositions of high activity in combination with other active ingredients such as allethrin, N-(chrysanthemoxymethyl)13,4,5,6-tetrahydrophthalimide (referred to as tetramethrin), 5-benzyl-3-furylmethyl chrysanthemate (referred to as Cryston, a registered trade mark of Sumitomo Chemical Co.), 3-phenoxybenzyl chrysanthemate, 5-propargylfurfuryl chrysanthemate and 2-methyl-5-propargyl-3-furylmethyl chrysanthemate; esters thereof, for example $\alpha$-trans-, and $\alpha$-cis,trans-chrysanthemic acid esters; pyrethrum extracts; $\alpha$-trans-, and $\alpha$-cis,trans-chrysanthemic acid esters of $\alpha$-allethrolone; other wellknown cyclopropanecarboxylic acid esters; organochlorine type insecticides, for example DDT, BHC and methoxychlor; organophosphorus type insecticides, for example 0,0-dimethyl-O-(3-methyl-4-nitrophenyl)-phosphorothioate (referred to as Sumithion, a registered trade mark of Sumitomo Chemical Co.), O,O-dimethyl-0-4-cyanophenylphosphorothioate (referred to as Cyanox, a registered trade mark of Sumitomo Chemical Co.) and O,O-dimethyl-0-(2,2-dichlorovinyl)-phosphate (referred to as LLVP); carbamate type insecticides, for example 1-naphthyl-N-methylcarbamate and 3,4-dimethylphenyl-N-methylcarbamate; other insecticides; microbial insecticides, for example fungicides, nematocides, acaricides, herbicides, plant regulators, fertilizer, B.T. and B.M.; insect hormone compounds; or other agricultural chemicals. Furthermore, a synergistic effect can also be expected.

Preparation of the present insecticides and acaricides and lethal effect thereof will be illustrated with reference to the following preparation examples, which are only given for the purpose of illustration and not to be interpreted as limiting.

Preparation 1

0.1 Part of each dl-trans isomer of the present compounds (1) to (8) was dissolved in kerosene to 100 parts of total weight. Eight oil sprays were thus obtained.

Preparation 2

0.05 Part of each d-trans isomer of the present compounds (1), (2), (4) and (7), and 0.25 part of piperonyl-butoxide were dissolved in kerosene to 100 parts of total weight. Four oil sprays were thus obtained.

Preparation 3

To 20 parts of each of the present compounds (1) to (8) were added 15 parts of Sorpol SM-200 (a registered trade mark of Toho Kagaku Co.) and 65 parts of xylene. The mixtures were each thoroughly mixed to make a solution. Eight emulsifiable concentrates were thus obtained.

Preparation 4

To 10 parts of each dl-trans isomer of the present compounds (3), (5), (6) and (8) were added 20 parts of S-421, 15 parts of Sorpol SM-200 (the same as above) and 55 parts of xylene. The mixtures were each thoroughly mixed to make a solution. Four emulsifiable concentrates were thus obtained.

Preparation 5

0.1 part of dl-trans isomer of the present compound (1) and 0.2 part of tetramethrin were dissolved in a mixture of 7 parts of xylene and 7.7 parts of deodorized kerosene. The solution was filled in an aerosol container. After attaching a valve portion to the container, 85 parts of propellant (e.g. liquefied petroleum gas) were charged therein under pressure through the valve. An aerosol was thus obtained.

Preparation 6

0.3 Part of dl-trans isomer of the present compound (7) and 0.1 part of 3-phenoxybenzyl-d-cis, trans-chrysanthemate were dissolved in a mixture of 7 parts of xylene and 7.6 parts of deodorized kerosene. The solution was filled in an aerosol container and then treated in the same manner as described in preparation 5. Thus an aerosol was obtained.

Preparation 7

0.2 Part of d-trans isomer of the present compound (2) and 0.1 part of allethronyl d-trans-chrysanthemate were dissolved in a mixture of 7 parts of xylene and 7.7 parts of deodorized kerosene. The solution was filled in an aerosol container and then treated in the same manner as described in Preparation 5. Thus an aerosol was obtained.

Preparation 8

0.5 g of each d-trans isomer of the present compounds (1), (2), (6), (7) and (8), and 0.5 g of BHT were dissolved in 20 ml of methanol. The solutions were each uniformly mixed with 99 g of mosquito coil carrier containing Tabu powder, Pyrethrum marc and wood powder in a ratio of 3 : 5 : 1, and then methanol was evaporated. To each residue was added 150 ml of water, kneaded thoroughly, shaped into a mosquito coil and dried. Five mosquito coils were thus obtained.

Preparation 9

0.15 g of each dl-trans isomer of the present compounds (3), (4) and (5), and 0.2 g of allethronyl d-trans-chrysanthemate were dissolved in 20 ml of methanol. The solutions were each uniformly mixed with 99.65 g of mosquito coil carrier (the same as above), and then methanol was evaporated. To each residue was added 150 ml of water, kneaded thoroughly, shaped into a mosquito coil and dried. Three mosquito coils were thus obtained.

Preparation 10

0.1 g of each d-trans isomer of the present compounds (1) and (7), 0.1 g of BHT and 0.1 g of piperonyl-butoxide were dissolved in a suitable amount of chloroform. The solutions were each adsorbed uniformly on filter paper of 3.5 cm × 1.5 cm in area and 0.3 cm in thickness.

Thus, two fibrous heating fumigant insecticidal compositions for use on a heater were obtained. Asbestos may be used as a fibrous carrier having the same effect, in place of pulp plate such as filter paper.

Preparation 11

0.02 g of d-cis,trans isomer of the present compound (7), 0.05 g of 5-propargyl-furyl-methyl-dl-cis,trans-chrysanthemate and 0.1 g of BHT were dissolved in a suitable amount of chloroform. The solution was adsorbed uniformly on filter paper of 3.5 cm × 1.5 cm in area and 0.3 cm in thickness. Thus, a fibrous heating fumigant insecticidal composition for use on a heater was obtained.

Preparation 12

20 Parts of each of the present compounds (1), (2) and (8), 10 parts of Sumithion (the same as above) and 5 parts of Sorpol SM-200 (the same as above) were thoroughly mixed. The mixtures were each mixed with 65 parts of 300 mesh talc in a mortar while thoroughly stirring. Three wettable powders were thus obtained.

Preparation 13

One part of each dl-trans isomer of the present compounds (4) and (7) and 2 parts of 1-naphthyl-N-methylcarbamate were dissolved in 20 parts of acetone, and then 97 parts of 300 mesh diatomaceous earth were added thereto. After thorough mixing in a mortar while stirring, acetone was removed by evaporation. Two dusts were thus obtained.

Preparation 14

3 Parts of each dl-trans isomer of the present compounds (1), (2), (4), (7) and (8), 5 parts of Toyolignin CT (a registered trade mark of Toyo Spinning Co.) and 92 parts of GSM Clay (a registered trade mark of Zieklite Mining Co.) were thoroughly mixed in a mortar.

Then the mixtures were each mixed with water of 10% by weight based on the mixture, granulated by means of a granulator and air-dried. Five granular preparations were thus obtained.

Preparation 15

Two parts of each of the present compounds (3) and (6), 2 parts of Cyanox (the same as above), 5 parts of Toyolignin CT (the same as above) and 91 parts of GSM clay (the same as above) were thoroughly mixed in a mortar.

Then the mixtures were each mixed with water in an amount of 10% by weight based on the mixture, granulated by means of a granulator and air-dried. Two fine granular preparations were thus obtained.

Preparation 16

0.1 Part of d-trans isomer of the present compound (2), 0.2 part of d-trans isomer of allethrin, 11.7 parts of deodorized kerosene and 1 part of Atmos 300 (a registered trade mark for an emulsifier sold by Atlas Chemical Co.) were thoroughly mixed, and emulsified by an addition of 50 parts of pure water. An aerosol container was then filled with the resulting emulsion and 35 parts of a 3 : 1 mixture of deodorized butane to deodorized propane. A water-based aerosol was thus obtained.

Preparation 17

3 Parts of d-trans isomer of the present compound (1) was dissolved in a suitable amount of acetone, and then the solution was adsorbed on 97 parts of solid food for mouse to obtain bait.

As a carrier for bait, there can be used various artificial solid diets which were prepared by mixing sugar, starch, rice-bran, grain powder and yeast; and mixtures of the diets and attractants for controlling injurious insects.

The biological effect of the insecticides and acaricides obtained according to the present invention is as follows.

EXAMPLE 1

5 ml of each of the oil sprays formulated according to Preparations 1 and 2 were sprayed, using Campbel's turn table method ("Soap and Sanitary Chemicals," Vol. 14, No. 6, 119, 1938). About 100 house-fly adults (*Musca domestica*) per group were exposed to the descending mist for 10 minutes. By the next day, more than 80% of the flies were killed with any oil spray.

EXAMPLE 2

The emulsifiable concentrates formulated according to Preparation 3 were each diluted 200,000 times with water. Two liters of each test emulsion so prepared were placed in a styrene case of 23 cm × 30 cm in area and 6 cm in depth, and about 100 full grown larvae of Northern house mosquito (*Culex pipens pullens*) were liberated therein. By the next day, more than 90% of the larvae were killed with any concentrate.

EXAMPLE 3

In 1/50,000 Wagner pots were grown rice plants which had elapsed 45 days after sowing. The emulsifiable concentrates formulated according to Preparation 3 were each diluted 200 times with water. Each test solution so prepared was individually sprayed on the rice plants in a proportion of 10 ml per pot. Each pot was covered with wire net and about 30 adults of green rice leaf-hoppers (*Nephotettix cincpiceps*) were libererated in the pot. After 1 day, more than 90% of the hoppers were killed.

EXAMPLE 4

Each of the emulsifiable concentrates formulated according to Preparation 4 was diluted 200 times with water. About 10 third to fourth instar larvae of tabacco cut worm (*Spodoptera litura*) were liberated in a glass Petri dish of 14 cm in inside diameter and 1 ml of each of dilute solutions was sprayed. Thereafter, the larvae were fed and allowed to stand in another dish, and after two days more than 90% of the larvae were killed with any concentrate.

EXAMPLE 5

The insecticidal activity on house-fly adults (*Musca domestica*) of the aerosols formulated according to Preparations 5, 6, 7 and 16 was tested by the aerosol test method ("Soap and Chemical Specialities, Blue Book", 1965) using a (6-ft)$^3$ Peet Grady's chamber. Thus, with any aerosol, more than 80% of the flies were knocked down 15 minutes after spraying and more than 70% of the flies were killed by the next day.

EXAMPLE 6

About 50 Northern house mosquito adults (*Culex pipens pullens*) were liberated in a (70-cm)$^3$ glass chamber in which a battery-type small fun (wing diameter 13 cm) was set and run. 0.1 g of each of the mosquito coils formulated according to Preparations 8 and 9 was ignited at one end and placed at the center of bottom of the chamber. With any mosquito coil, more than 90% of the adults were knocked down within 20 minutes and more than 80% of the adults were killed by the next day.

EXAMPLE 7

About 50 house-fly adults (*Musca domestica*) were liberated in a (70-cm)³ glass chamber in which a battery-type small fan (wing diameter 13 cm) was set and run. Each of heating fumigant compositions formulated according to Preparations 10 and 11 was placed on a heater in the chamber and smoken. More than 90% of the adults were knocked down within 20 minutes with any fumigant.

EXAMPLE 8

About 20 rice plants were grown up to a 3 to 4-leave stage in a flower pot of 10 cm in diameter, and then a 200-fold aqueous diluted solution of each wettable powder formulated according to Preparation 12 was applied thereto by means of a turn table. After airdrying, each pot was covered with a wire cage and 20 to 30 smaller brown planthopper adults (*Laodelphax striatellus*) were liberated therein. The dead and alive after 24 hours were counted and more than 80% mortality was obtained.

EXAMPLE 9

A glass Petri dish of 14 cm in inside diameter was coated on the inside wall with butter, leaving at the lower part an uncoated portion of 1 cm in width. Onto the bottom of the dish, each of the dusts formulated according to Preparation 13 was uniformly dusted in the proportion of 2 g/m².

subsequently, 10 German cockroach adults (*Blattella germanica*) per group were liberated in the dish and allowed to come into contact with the dust for 30 minutes. After 3 days, more than 90% of the knocked down adults were killed.

EXAMPLE 10

Ten liters of water were placed in a 14 liter polypropylene bucket, and 1 g of each of the granular preparation formulated according to Preparations 14 and 15 was added thereto. After 1 day, about 100 full grown Northern house mosquito larvae (*Culex pipens pullens*) were ilberated in the water. More than 90% of the larvae were killed within 24 hours.

EXAMPLE 11

Rice plants were grown up to the tillering stage in a 1/100,000 Wagner's pot and water depth was keep 5 cm. Each of the granular preparations formulated according to Preparation 14 was applied thereto in the proportion of 10 kg/10 ares. Thereafter, the pots were covered with a wire cage and smaller brown planthopper adults (*Laodelphax striattelus*) were liberated therein. After 24 hours, more than 90% of the adults were killed with any granular preparation.

EXAMPLE 12

Three grams of each of the oil sprays formulated according to Preparation 2 were fogged, by means of an insect fogger (Burgess Vibrocrafters INC., U.S.A.), into a Peet Grady's chamber (the same as in Example 5) in which about 500 house-fly adults (*Musca domestica*) had previously been liberated. After 30 minutes, more than 90% of the adults were knocked down.

EXAMPLE 13

Armyworms and cutworms, cabbage worm and diamond-back moth were artificially made parasitic on chinese cabbage which had been grown up in a greenhouse. Then the house (2 m in height) was divided into spaces (30 m² in area, 2 m in height), and 10 g of each of the wettable powders formulated according to Preparation 12 were smoken in SEARCH in each divided space. The spread of damage by the insects was hardly observed with any wettable powder.

EXAMPLE 14

Carmine mite females (*Tetranychus telarius*) were made parasitic on leaves of the potted kidney bean (two-leave stage) which had elapsed 9 days after sowing, in a proportion of 10 – 15/leaf, and bred at 27°C for a week in a constant temperature room. Then numerous carmine mites were found to be bred at various growth stages. At this time, a 200-fold aqueous dilute solution of each emulsifiable concentrate formulated according to Preparation 3 was sprayed in a proportion of 10 ml/pot by means of a turn table. After 10 days, damage of kidney bean by the insects was hardly observed.

EXAMPLE 15

Ten German cockroach adults (*Blattella germania*) were liberated in a glass Petri dish and absorbent cotton containing water and 1 g of bait formulated according to Preparation 17 was placed therein. After 7 days, all the cockroach adults were killed.

What we claim is:

1. A compound of the formula,

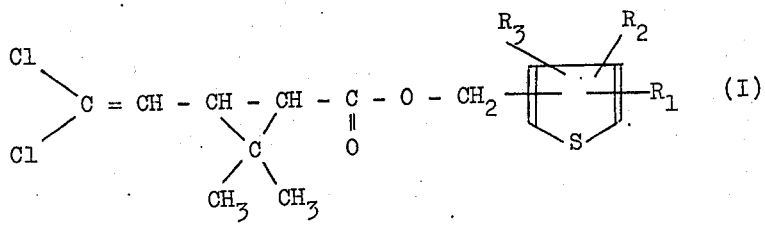

wherein $R_1$ is alkyl having up to four carbon atoms, alkenyl having up to five carbon atoms, cycloalkenyl having up to six carbon atoms, alkynyl having up to five carbon atoms, benzyl, phenoxy or halogen; $R_2$ and $R_3$ are hydrogen, halogen or methyl; and any adjacent two of $R_1$, $R_2$ and $R_3$ may conbine to form polymethylene.

2. A compound of the formula,

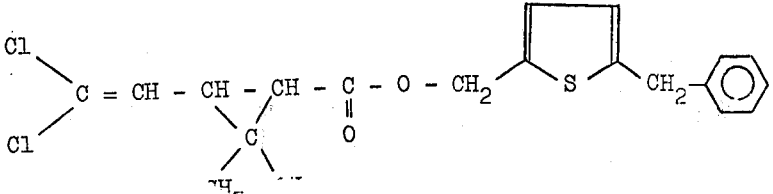

3. A compound of the formula,
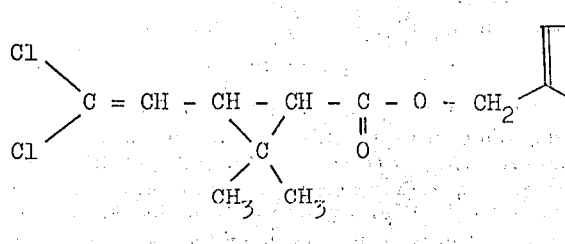
* * * * *